United States Patent [19]
Moeggenborg et al.

[11] Patent Number: 6,060,318
[45] Date of Patent: May 9, 2000

[54] TRACING OF PROCESS ADDITIVES IN INDUSTRIAL CERAMICS APPLICATIONS

[75] Inventors: Kevin J. Moeggenborg; James E. Whitten, both of Naperville; Joseph C. Alfano, Lisle, all of Ill.

[73] Assignee: Nalco Chemical Company, Naperville, Ill.

[21] Appl. No.: 09/223,868

[22] Filed: Dec. 31, 1998

Related U.S. Application Data

[60] Division of application No. 08/877,452, Jun. 17, 1997, abandoned, which is a continuation-in-part of application No. 08/873,046, Jun. 11, 1997, abandoned.

[51] Int. Cl.$^7$ .................................................. G01N 21/64
[52] U.S. Cl. .................................. 436/3; 436/52; 436/55; 436/172; 436/177
[58] Field of Search .................................. 436/3, 52, 55, 436/172, 177

[56] References Cited

U.S. PATENT DOCUMENTS

| | | |
|---|---|---|
| 4,992,380 | 2/1991 | Moriarty et al. . |
| 5,168,082 | 12/1992 | Matchett et al. . |
| 5,304,800 | 4/1994 | Hoots et al. . |
| 5,324,770 | 6/1994 | Cosper . |
| 5,350,549 | 9/1994 | Boyle . |

FOREIGN PATENT DOCUMENTS

| | | |
|---|---|---|
| 4300723C2 | 11/1993 | Germany . |
| 197 09 377 A1 | 3/1997 | Germany . |

OTHER PUBLICATIONS

Smith et al., "High Precision Fluorimetry with a Light–Emitting Diode Source," Appl. Spectroscopy vol. 42, 1469–1472 (1988).

Imasaka et al., "Visible Semiconductor Laser Fluorometry," Anal. Chem. 61, 2285–2288 (1989).

Patonay et al., "Semiconductor Lasers in Analytical Chemistry," Proceedings of SPIE–The International Society for Optical Engineering vol. 1435, 52–63 (1991).

Higashijima et al., "Determination of Amino Acid by Capillary Zone Electrophoreses Based on Semiconductor Laser Fluorescence Detection," Anal. Chem. 64, 711–714 (1992).

Mank et al., "Visible Diode Laser Induced Fluorescence Detection in Liquid Chromatography after Precolumn Derivatization of Thiols," Anal. Chem. 65, 2197–2203 (1993).

Hauser et al., A Solid–State Instrument for Fluorescence Chemical Sensors Using a Blue Light–Emitting Diode of High Intensity, Meas. Sci. Technol. 6, 1081–1085 (1995).

Wengatz et al., "Immunoassays for Pesticide Monitoring," Proceedings of SPIE–The International Society for Optical Engineering 2388, 408–416 (1995).

Williams et al., "Instrument to Detect Near–Infra Red Fluorescence in Solid–Phase Immunoassay," Anal. Chem. 66, 3102–3107 (1994).

Kawazumi et al., "Laser Fluorometry Using A Visible Semiconductor Laser and an Avalanche Photodiode for Capillary Electrophoresis," Anal. Sci. 11, 587–590 (1995).

Montan et al., "A System for Industrial Surface Monitoring Utilizing Laser–Induced Fluorescence". Appl. Phys. B38, 241–247 (1985).

Winkleman et al., "Quantitative Fluorescence Analysis in Opaque Suspensions Using Front Face Optics," Anal. Chem. 39, 1007–1009 (1967).

Hakkanen et al., "Laser–Induced Fluorescence Imaging of Paper Surfaces," Appl. Spectroscopy 47, 2122–2125 (1993).

T. Araki and H. Misawa, "Light–Emitting Diode–Based Nanosecond Ultraviolet Light Source for Fluorescence Lifetime Measurements," Rev. Sci. Instrum. 66 (12), pp. 5469–5472 (1995).

*Primary Examiner*—Jeffrey Snay
*Attorney, Agent, or Firm*—Margaret M. Brumm; Thomas M. Breininger

[57] ABSTRACT

The present invention provides for an improved method for monitoring the concentration of molecules and chemical treatment agents in ceramic slurries and powders.

19 Claims, 5 Drawing Sheets

6,060,318

TRACING OF PROCESS ADDITIVES IN INDUSTRIAL CERAMICS APPLICATIONS

CROSS-REFERENCE TO RELATED PATENT APPLICATIONS

The present patent application is a divisional of U.S. patent application Ser. No. 08/877,452, filed Jun. 17, 1997, now abandoned, which is a continuation-in-part of U.S. patent application Ser. No. 08/873,046, filed Jun. 11, 1997, now abandoned, by Joseph C. Alfano, Michael J. Fehr, Martin R. Godfrey, John E. Hoots, Narasimha M. Rao, Karen R. Tubergen and James E. Whitten, entitled "Using an All Solid-State Fluorometer and a System and Method for Using in Industrial Water System Applications", the disclosure of which is incorporated herein by reference.

BACKGROUND OF THE INVENTION

1. Field of the Invention

The present invention generally relates to systems and methods for continuously monitoring controlling the concentration of molecules or chemical species in a ceramic slurry or powder. More specifically, the present invention relates to systems and methods for monitoring the concentration of tracer molecules or tagged organic additive molecules in a ceramic slurry or powder. Further, the present invention relates to use of fluorometer, or ion selective electrode for monitoring the concentration of fluorescent tracer molecules in a ceramic slurry or powder.

2. Description of the Prior Art

It is generally known to use diode lasers or light-emitting diodes (LED) as solid-state excitation sources for fluorescence. The combination, however, of excitation sources with photodiode detectors is not as common. As early as 1988, a fluorometer from an LED and a photodiode detector was constructed. See, for example, an article by Jones et al. entitled "High Precision Fluorimetry with a Light-Emitting Diode Source," *Appl. Spectroscopy* 42, 1469 (1988). In 1989, a 670 nanometer diode laser was used as an excitation source and a photomultiplier (PMT) as a detector. See Imasaka et al. "Visible Semiconductor Laser Fluorometry," *Anal. Chem.* 61, 2285 (1989). Other examples are known in which semiconductor lasers have been combined with conventional PMT detectors. See, for example, Patonay et al. "Semiconductor Lasers in Analytical Chemistry," *Proceedings of SPIE—The International Society for Optical Engineering* 1435, 42 (1991); Higashijima et al. "Determination of Amino Acid By Capillary Zone Electrophoresis Based on Semiconductor Laser Fluorescence Detection," *Anal. Chem.* 64, 711 (1992); and Mank et al. "Visible Diode Laser Induced Fluorescence Detection in Liquid Chromatography after Precolumn Derivatization of Thiols," *Anal. Chem.* 65, 2197 (1993).

In addition, several more recent publications have dealt with fluorescence measurements using LEDs or diode lasers as excitation sources and silicon photodiodes as detectors. See, for example, Hauser et al., "A Solid-State Instrument for Fluorescence Chemical Sensors Using a Blue Light Emitting Diode of High Intensity," *Meas. Sci. Technol.* 6, 1081 (1995); Wengatz et al., "Immunoassays for Pesticide Monitoring," *Proceedings of SPIE—The International Society for Optical Engineering* 2388, 408 (1995); Williams et al., "Instrument to Detect Near-Infra-Red Fluorescence in Solid-Phase Immunoassay," *Anal. Chem.* 66, 3102 (1994); and Kawazumi et al., "Laser Fluorimetry Using A Visible Semiconductor Laser and an Avalanche Photodiode for Capillary Electrophoresis," *Anal. Sci.* 11, 587 (1995).

Of the above, most of the few known literature references demonstrate the principle of fluorometry using solid-state, low cost excitation sources. Only a few of the existing papers, however, deal with applications of this instrumentation. For example, Higashijima et al. generally disclose the use of fluorescence detectors for electrophoresis; Mank et al. generally disclose the use of fluorescence detectors for liquid chromatography; and Hauser et al. relate to use of fluorescence detectors for chemical-sensing membranes. In addition, Wengatz et al. explore the use of fluorescence detectors for pesticide monitoring.

A number of other techniques are known for monitoring fluorescence, for example, from oil residues on steel sheets (such as taught by Montan et al. in "A System for Industrial Surface Monitoring Utilizing Laser-Induced Fluorescence," *Appl. Phys.* B38, 241 (1985)) and for fluorescence analysis of biologically important molecules in turbid or opaque tissue samples (for example, as demonstrated by Winkleman et al. in "Quantitative Fluorescence Analysis in Opaque Suspensions Using Front Face Optics," *Anal. Chem.* 39, 1007 (1967)). Furthermore, use of an excimer laser to perform fluorescent imaging of paper surfaces is generally taught by Hakkanen et al. in "Laser-Induced Fluorescence Imaging of Paper Surfaces," *Appl Spectroscopy* 47, 2122 (1993); and use of a diode laser in surface fluorescence geometry is also generally taught, for example, by German Patent No. DE4300723 A1.

Fluorometers currently being used for industrial process monitoring and control are based on gas-lamp excitation sources and photomultiplier tube detectors which require high current, high voltage power supplies. Additionally, these excitation and detection sources do not have the intrinsic reliability of solid-state semiconductor devices.

A need, therefore, exists for an improved instrument constructed as an all solid-state fluorometer including a system and method for the use of such a fluorometer for monitoring the concentration of fluorescent tracer molecules particularly in a ceramic slurry.

SUMMARY OF THE INVENTION

The present invention provides for an improved method for monitoring the concentration of molecules and chemical treatment agents in ceramic slurries and powders.

To this end, in a preferred embodiment of the present invention, a device is provided having a solid-state excitation source to direct light in a specified direction. A sample having a known concentration of molecules is provided wherein the light from the excitation source is directed at the sample such that the light excites fluorescent tracer molecules in the sample and produces fluorescence. A detector receives the fluorescence from the excitation of the sample and produces an output signal proportional to the quantity of fluorescence received on the detector wherein the quantity of fluorescence is further proportional to the concentration of the molecules in the sample. If the concentration of the fluorophore is proportional to non-fluorescing chemical treatments or additives, then the concentration of the chemical treatments or additives can be monitored.

A lens, though not crucial, may alternatively be provided between the sample and the detector to image the fluorescence excited from the sample onto the detector. In an alternative embodiment, a filter is constructed and arranged between the sample and the detector to reject scattered excitation light from the sample or sample cell.

In a further embodiment, an amplifier is constructed and arranged to receive the signal from the detector to produce an amplified output signal. In a further embodiment, a battery provides power necessary to activate the excitation source and detector circuitry. The excitation source may be a diode laser or a light emitting diode or other solid-state light sources. Alternatively, DC power from an AC-DC transformer provides power necessary to activate the excitation source and detector circuitry.

Under one embodiment, the tracer molecules are fluorophores. In a further embodiment, the monitoring is conducted in real time.

Still further, the excited light may be filtered from the sample before detecting fluorescence.

In an embodiment, the amplified output signal is indicative of the fluorescence.

In an embodiment, power is provided to the instrument such that the power allows for portability of the instrument.

In an embodiment, the excitation source is separated from a point at which detecting occurs such that the components are approximately at a 90° angle with respect to each other. This angle is favored in embodiments where a turbid ceramic slurry is first centrifuged and the supernatant is then analyzed with a flourometer.

In another embodiment, the excitation source is separated from a point at which detection occurs such that the components are approximately at a 45° angle with respect to each other. This allows fluorescence to be detected from turbid or opaque samples, since it is not necessary for the excitation light to penetrate the sample. This embodiment is useful for turbid streams such as ceramic slurries and powders containing high masses of solids.

In an embodiment in which the excitation source and detector are separated by 45°, multiple filters may be used to suppress scattered excitation light. The polarized nature of diode laser light may also be taken advantage of to reject scattered excitation light by using cross-polarization in the detection path.

In an embodiment, multiple excitation sources and detectors may be stacked to measure a corresponding number of multiple analytes in the sample stream.

In yet another embodiment, the solid-state excitation source is pulsed to enable measurement of the fluorescent or phosphorescent lifetimes of chemical species in the ceramic slurry or powder.

In an embodiment, the solid-state excitation source is pulsed to enable higher peak output power at a given spectral region without damaging the excitation source.

In an embodiment, the excitation source is pulsed and the detector circuitry is "phase-locked" to the frequency of the excitation source to achieve higher sensitivity or to differentiate between multiple excitation sources.

In an embodiment, the concentration of a non-fluorescing chemical treatment or additive can be measured and controlled when it is fed in known proportion to a fluorescing tracer agent which can be directly measured and controlled by the fluorometer.

In a further embodiment, near-infrared emitting diode lasers or LEDs are used to excite fluorescence.

In an embodiment, treatment dosage to the sample stream is controlled based on the concentration of molecules detected by the instrument.

In an embodiment, the output signal is monitored continuously and in real time to determine the concentration of molecules.

In one embodiment, leakage to or from a ceramic slurry or powder is detected by detecting the concentration of molecules into or from a process, respectively.

In an embodiment, the inert tracer molecule may be a cationic or anionic species and the detection device may be an ion selective electrode specific for the inert ionic tracer.

Additional features and advantages of the present invention are described in, and will be apparent from, the detailed description of the presently preferred embodiments and from the drawings.

The invention detailed in this application is distinct from the prior art, in that it provides for the use of all solid-state fluorometers for use in monitoring and control of treatment agents used in ceramic slurries or powders. While prior art discloses the design and construction of fluorometers for fluorescent measurements, it does not teach the use of this technology for monitor and control of ceramic slurries or powders.

DESCRIPTION OF THE PREFERRED EMBODIMENTS

Figure 1:
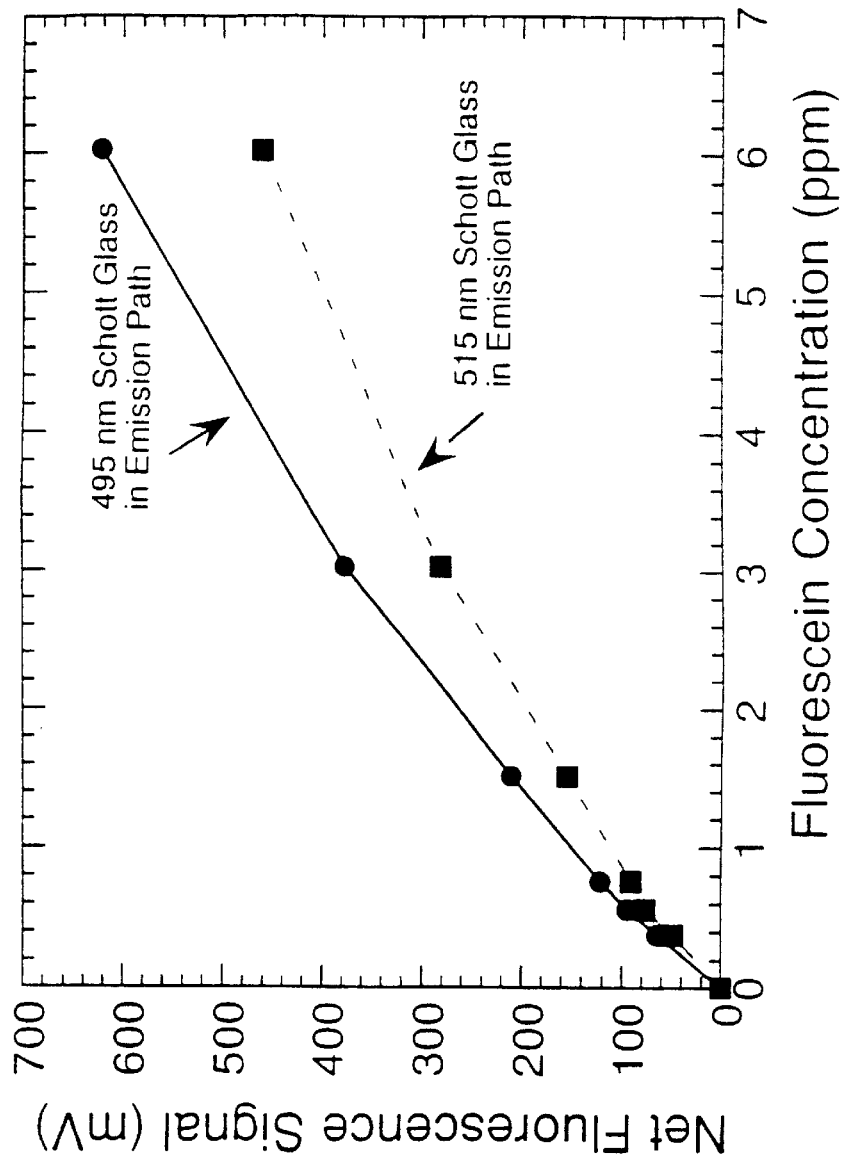
FIG. 1 illustrates a graph comparing data obtained using a Panasonic 450 nm high brightness blue light-emitting diode and fluorescein in an alumina slurry. Results from two different runs are shown, with the difference between the two being the choice of Schott glass emission filter.

The present invention generally relates to the use of all solid-state fluorometers in ceramic slurries or powders. More specifically, the present invention relates to use of diode laser-based or light-emitting diode-based fluorometers or ion selective electrodes to monitor tracers or the concentration of tracer molecules in ceramic slurries or powders.

A number of different process additives are used in the production of ceramic materials. Binders, plasticizers, dispersants, pressing aids (lubricants), and antifoams are among the organic additives used in ceramic applications. Additionally, small amounts (<10%) of inorganic additives or dopants may be added to improve the sintering, mechanical, or electrical properties of the ceramic material. In many cases, knowledge and control of the exact dosages and uniform distribution of these additives is critical to the quality of the final ceramic product. As such, dosages of these materials must be closely monitored and controlled. Present methods to measure such dosages are very time consuming, laborious and, usually, not specific for a single additive. The invention comprises the use of tracing methods to determine the concentrations of these additives in ceramic slurries or, in some cases, in ceramic powders and green bodies.

The most common method currently employed to trace the concentration of organic additives in ceramic slurries is the loss on ignition (LOI) method. This method requires that a slurry sample be dried and the residue accurately weighed.

The residue is then heated to combust the organic components of the residue. Organic additive content is then calculated from the weight loss after heating. This method is very time consuming (typically 5–7 hours) and is not specific to a single additive. Only the total organic additive content can be determined. Additionally, some ceramic raw materials, such as clays, contain organic species as natural components of the material. The LOI method does not distinguish between this raw material component and organic process additives. As such, the LOI method can be misleading even to the total amount of process additives in a slurry.

One method employed by the present invention to trace the concentrations of a fluorescent molecule in ceramic slurries requires the passage of light though the sample to be measured. Due to the opacity of a ceramic slurry, it is necessary to first centrifuge down the majority of the slurry solids before the fluorescence can be measured. Although effective, this method is not as efficient as the preferred method of the invention, due to the need of a centrifuge for the test.

The preferred method of the invention measures fluorescence without light penetrating the bulk of the sample. The angle between the excitation and emission light beams is much less than 90 degrees, and fluorescence is detected from the surface of the fluorescent slurry. The excitation sources used consist preferably of light-emitting diodes or semiconductor diode lasers. These devices have advantages of low cost, high optical output, monochromaticity, solid-state reliability, and the ability to run on batteries. It should be noted, however, that the excitation source is not necessarily limited to these types of devices.

Since the ceramic slurry is turbid and opaque, most of the light is quickly scattered before it can penetrate deeply into the cell, and only the fluorophores near the front surface of the cell are excited. The fluorescence is collected with a lens and imaged onto a detector. Preferably, a silicon photodiode detector is used. However, a photomultiplier tube or other detector could also be employed. Preferably, one or more filters or polarizers are used in the light path to prevent scattered excitation light from impinging on the photodiode detector. The output from the photodiode is amplified by a precision FET-input operational amplifier which produces an output voltage proportional to the quantity of fluorescence striking the photodiode.

The fluorescence striking the detector is proportional to the concentration of an inert fluorophore present in the ceramic slurry. Continuous monitoring of this voltage output is possible and allows realtime measurement of the concentration of a fluorescent tracer present in the slurry. This instrument therefore permits either grab sample measurements or continuous on-line monitoring of a ceramic treatment agent which is fluorescent or a treatment agent to which a known concentration of an inert, fluorescent tracer molecule has been added. Furthermore, the voltage output of the detector can be compared to preset values, either electronically or with a microcomputer, and used to alter dosage of the treating agent.

Figure 2:
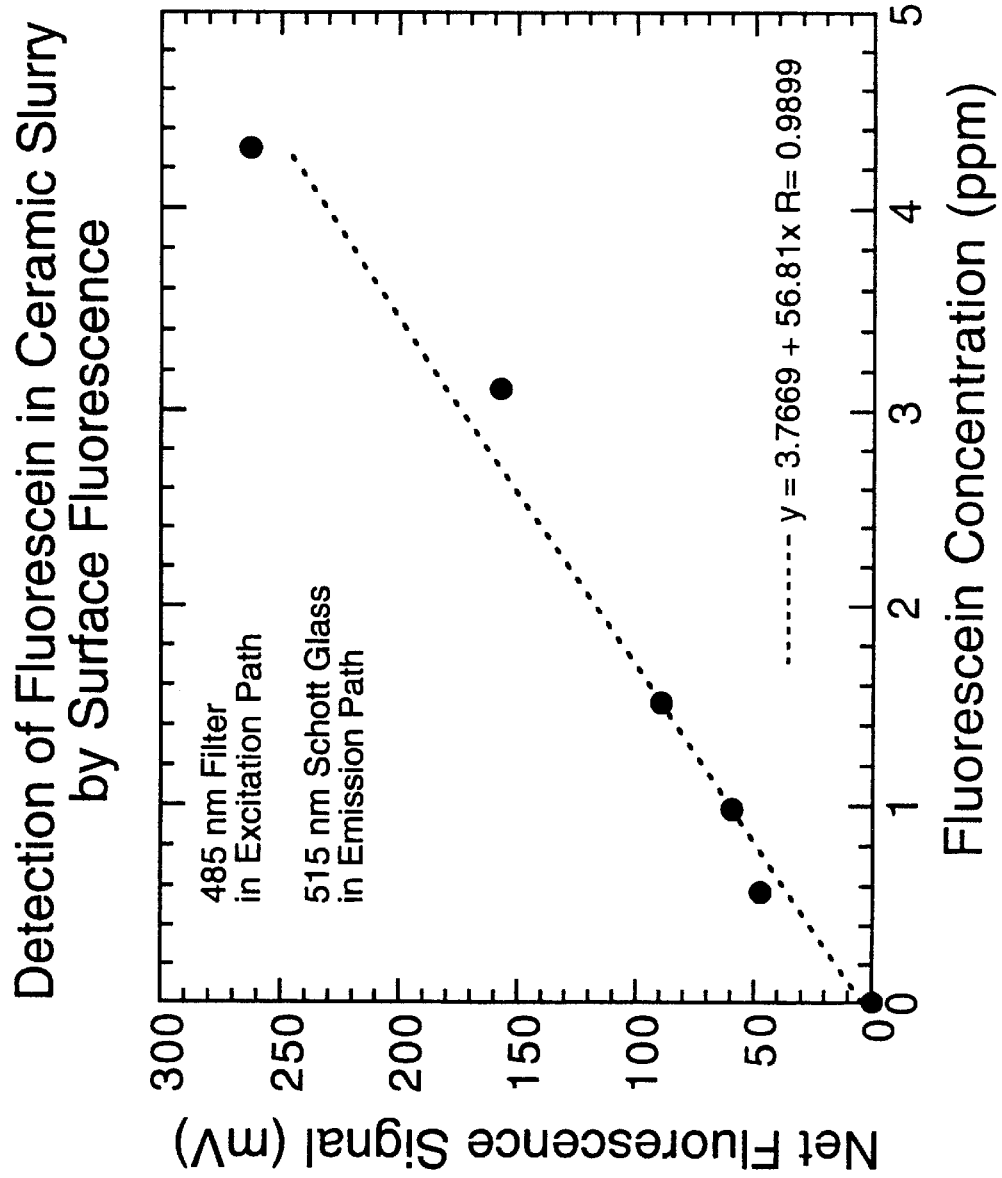
FIG. 2 illustrates a graph similar to FIG. 1 and where the concentration of fluorescein in the slurry is varied. Results from two different runs are shown, with the difference between the two being the choice of Schott glass emission filter.

FIG. 1 shows data obtained using a Panasonic 450 nm high brightness blue light-emitting diode and a suitable fluorophore, fluorescein, in an alumina slurry. The concentration of the fluorescein in the slurry was varied and fluorescence measurements were made. Results from two different runs are shown, with the difference between the two being the choice of Schott glass emission filter. FIG. 2 shows similar data for fluorescein detection in a slurry made from a high purity alumina containing a green dye.

LEDs are commercially available which emit at wavelengths longer than ~400 nm. Diode lasers emitting light at wavelengths of 635 nm and longer are commercially available, and ones at wavelengths as short as 415 nm have been demonstrated. As solid-state technology advances, an even wider variety of fluorescent molecules will be accessible.

In addition to tracing by use of a fluorescent molecule, it is possible to follow additive concentrations using other tracer molecules. Ion selective electrodes are available which can track specific ions to the low ppm range. Use of a bromide selective electrode, for example, along with a bromide salt as the tracer molecule allows the user to obtain the same type of information as is available through the fluorescence technique. An ion-selective electrode is especially advantageous in working with slurries that have been dyed to distinguish between different slurry grades. Since these dyes can interfere with fluorophores, the ion-selective electrode provides an alternative method of monitoring and control.

The method of the invention will allow the concentration of ceramic process additives to be determined in a ceramic slurry or, in some cases, powder or green body. Additionally, the technique could be used to determine the amount of mixing time needed to assure uniform distribution of these additives in a mixing vessel. An adaptation of the technique will allow the user to determine batch to batch contamination from ball mills and other mixing vessels, and the efficiency of transfer from the mill and mix tanks. Still further, it is possible to study the extent of migration of small molecules to the granulate surface during spray drying. The fluorescence of the dry powder is measured in the surface mode, to determine relative concentrations of the tracer on the granulate surface.

Figure 3:
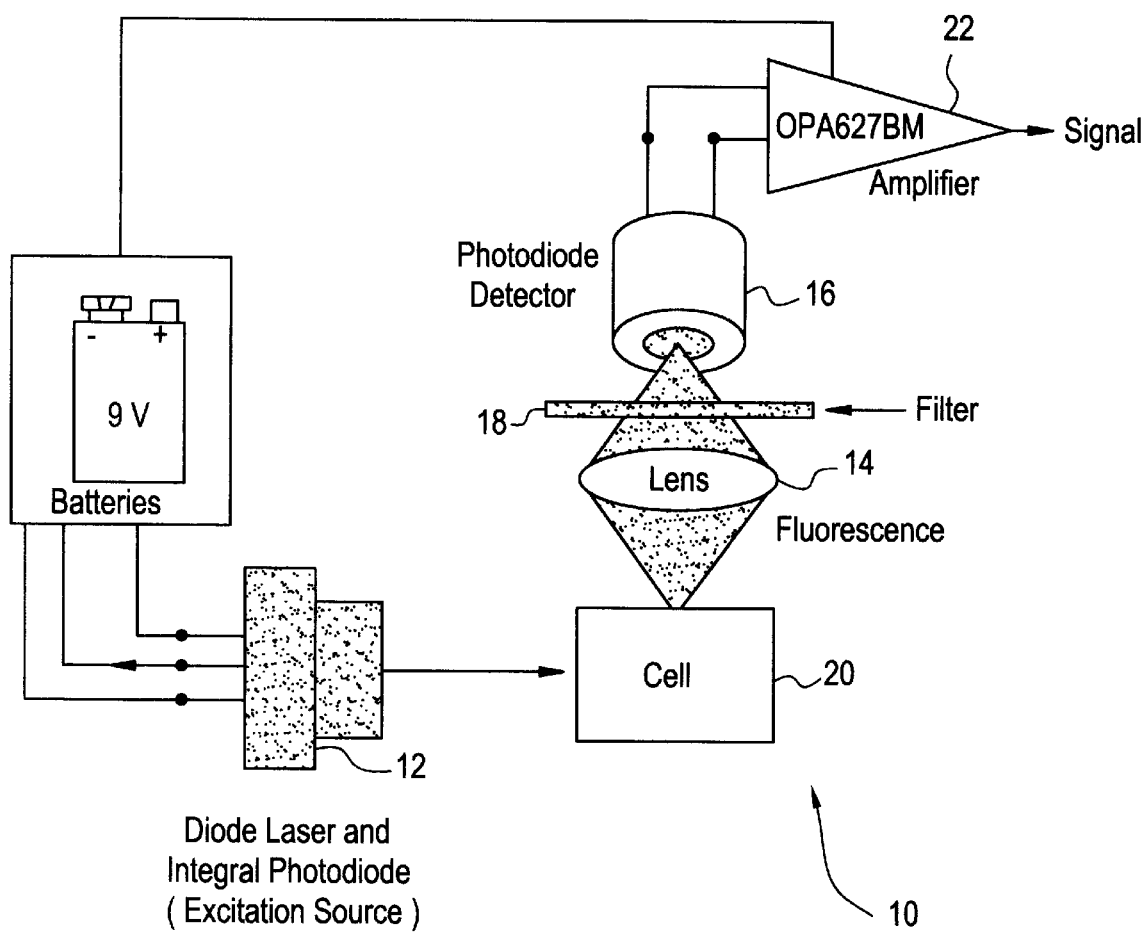
FIG. 3 illustrates a schematic diagram of an embodiment of a fluorometer, using a diode laser excitation source.

Referring now to FIG. 3, a schematic of an instrument 10 of the present invention is generally illustrated. In the instrument 10, a solid-state diode laser including an integral photodiode 12 is used as an excitation source to excite fluorescent tracer molecules. It should be understood that solid-state lasers emitting visible and near-infrared radiation are presently available and may be incorporated by those skilled in the art.

Fluorescence resulting from excitation of the diode laser 12 may be imaged with a lens 14 onto a silicon photodiode detector 16. (Throughout this disclosure, the term "fluorescence" is meant to encompass both fluorescence and phosphorescence.) An optical filter 18 may be placed between a sample cell 20 and the photodiode detector 16 to reject scattered laser light. An output from the photodiode detector 16 may be amplified by a precision FET-input operational amplifier 22 which is capable of producing an output voltage signal proportional to the quantity of fluorescence-striking the photodiode detector 16.

Since this fluorescence is proportional to the concentration of a fluorophore present in a ceramic slurry or powder, continuous monitoring of a voltage output is possible, and real time measurement of the concentration of a fluorescent tracer present in the slurry or powder may be ascertained. Furthermore, the voltage signal from the detector 16 may be compared to pre-set values. Such a comparison may take place either electronically or via a microcomputer. With such comparisons, the voltage signal may be used to control a pump relay which is capable of controlling the dosage of a treating agent containing an inert tracer.

Preferably, fluorescein is used as an additive. Blue light-emitting diodes are presently available which make construction of a solid-state fluorometer for fluorescein possible. Blue diode lasers may be used to greatly increase the sensitivity of the solid-state fluorometer. A laser-based instrument could also be combined with a miniature photomultiplier tube to provide orders of magnitude more sensitivity than existing instrumentation.

The detection limit for a rhodamine 800 dye with the instrument 10 is measured to be 1.5 ppb which is sufficient for the types of applications set forth above. Another example of a fluorescent compound is methylene blue. The instrument 10 has sufficient sensitivity to measure methylene blue concentrations as low as 10 ppb. Many other dyes may also be implemented which are suitable for fluorescent tracer measurements.

Figure 4:
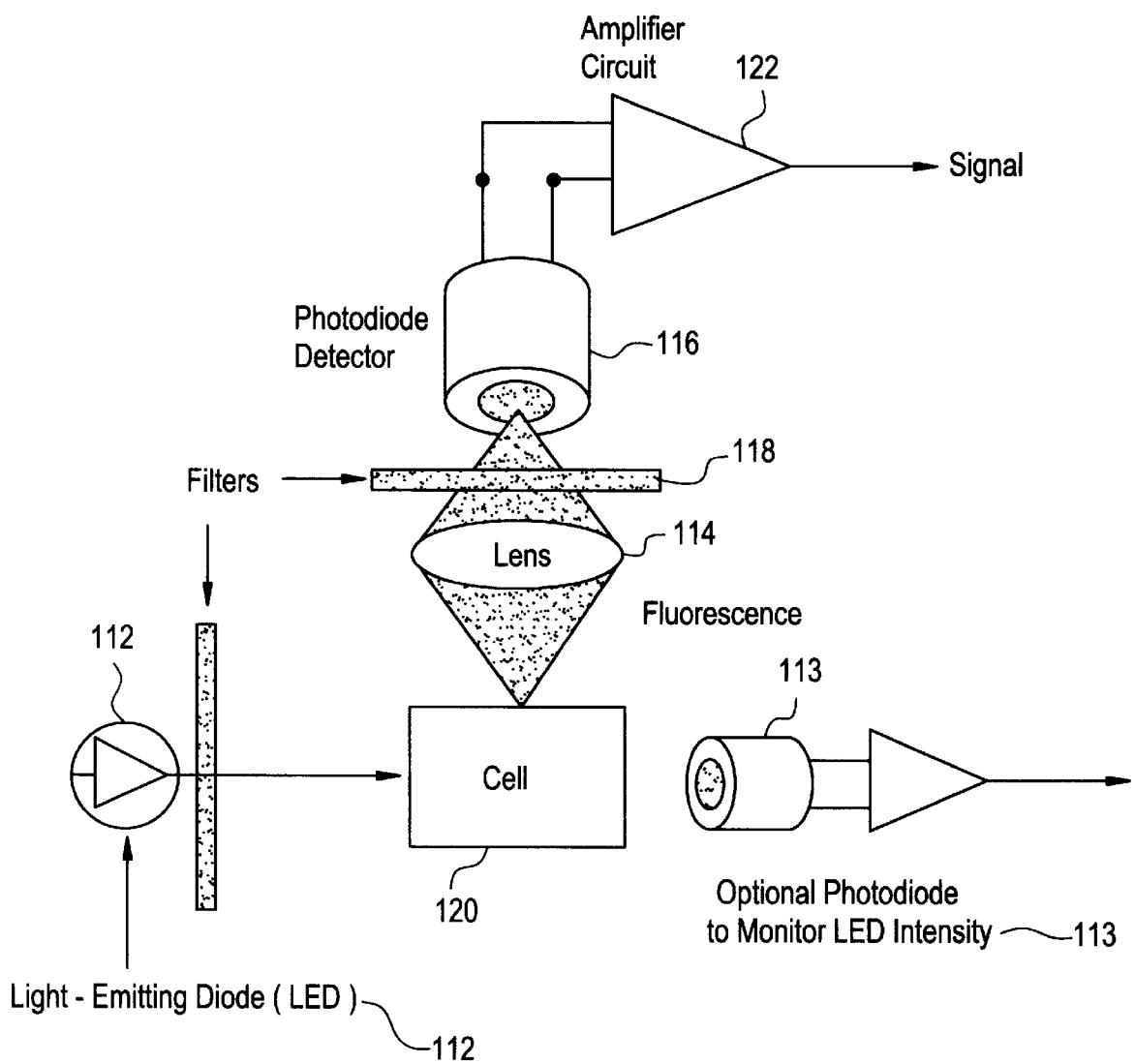
FIG. 4 illustrates a schematic diagram of the embodiment of a fluorometer, using a light-emitting diode as an excitation light source.

FIG. 4 is a schematic of an embodiment of the present invention in which a light-emitting diode 112 is used as an excitation source. Unlike diode lasers, light-emitting diodes do not have integral photodiodes to monitor and stabilize their optical output. In some cases, as shown in FIG. 4, it may be necessary to use an external photodiode 113 to monitor an output of the light-emitting diode and normalize the fluorescence intensity to variations in its output. This photodiode can also serve as a monitor of optical fouling of the flow cell and can be used to indicate when the cell needs to be cleaned. An optical filter 118 is placed between the light-emitting diode 112 and a sample in order to remove components of the optical output that are at the same wavelength as the fluorescence. Other components of the instrumentation are the same as for FIG. 3.

In addition to using light-emitting diodes to emit their specified radiation, in some cases LEDs may be used in an unconventional fashion as novel ultraviolet (UV) light sources. Blue LEDs operating at higher than specified forward currents have been found to emit a portion of their optical output in the near-UV region of the spectrum, i.e., in the range of from about 370 nm to about 500 nm. For example, T. Araki and H. Misawa ["Light-Emitting Diode-Based Nanosecond Ultraviolet Light Sources for Fluorescence Lifetime Measurements," Rev. Sci. Instrum. 66,5469 (1995)] have shown that a nominal 450 nm InGaN/AlGaN LED operating at currents greater than 50 mA emits a 380 nm satellite peak which grows in intensity with increasing current.

Satellite emissions of 380–390 nm have been observed from a variety of blue LEDs at higher than specified operating currents and voltages. This satellite peak may be used to excite fluorescence from near-UV absorbing fluorophores such as pyrene tetrasulfonic acid (PTSA). The LED may either be operated in continuous or pulsed mode. The pulsed mode may be desirable to extend the lifetime of the LED or to allow higher peak optical output to be achieved.

Since the instrument 10 of the present invention is solid-state, this instrument 10 has extremely high reliability. Operating lifetimes of diode lasers are typically between 20,000 to 40,000 hours, which are several times higher than that of gas discharge lamps. Additionally, due to the solid-state nature of the components, the design of the instrument 10 is simpler than conventional instruments and assembly costs are minimal.

The detection limit for rhodamine 800, a red-absorbing fluorophore, was measured at 1.5 ppb with the diode laser fluorometer instrument 10 of the present invention as set forth above. Detection limits for other known fluorometers, such as Hitachi's F4500 Research Fluorometer, is approximately 5 ppb, higher than that of the present invention. Therefore, due to the high sensitivity of the photodiode detector to red light, as well as the high optical efficiency of using monochromatic lasers for an excitation source, the diode laser fluorometer instrument 10 of the present invention has excellent sensitivity. Preferably, the diode laser uses a near infrared wavelength of from about 635 nm to about 1600 nm.

Still further, the small size of the light source and detector of the present invention lends the diode laser fluorometer instrument 10 to multi-channel, multi-analyte detection. A ceramic slurry or powder may contain several fluorescent tracers, and an array of two or more diode lasers of different wavelengths could simultaneously monitor several tracers as the sample stream passes through the flow cell. This type of multi-channel detection is more difficult to achieve using current technology.

Furthermore, an embodiment of the invention in which the excitation and detection of fluorescence occurs from the front surface of the sample cell makes it possible to perform measurements in sample streams of high turbidity such as ceramic slurries.

By separating the excitation source and detector by 45°, fluorescence can be measured from the surface of the opaque sample or slurry. The coherence and polarization of a laser beam allows the surface fluorometry to be performed much more conveniently and compactly than is possible with conventional excitation sources.

Figure 5:
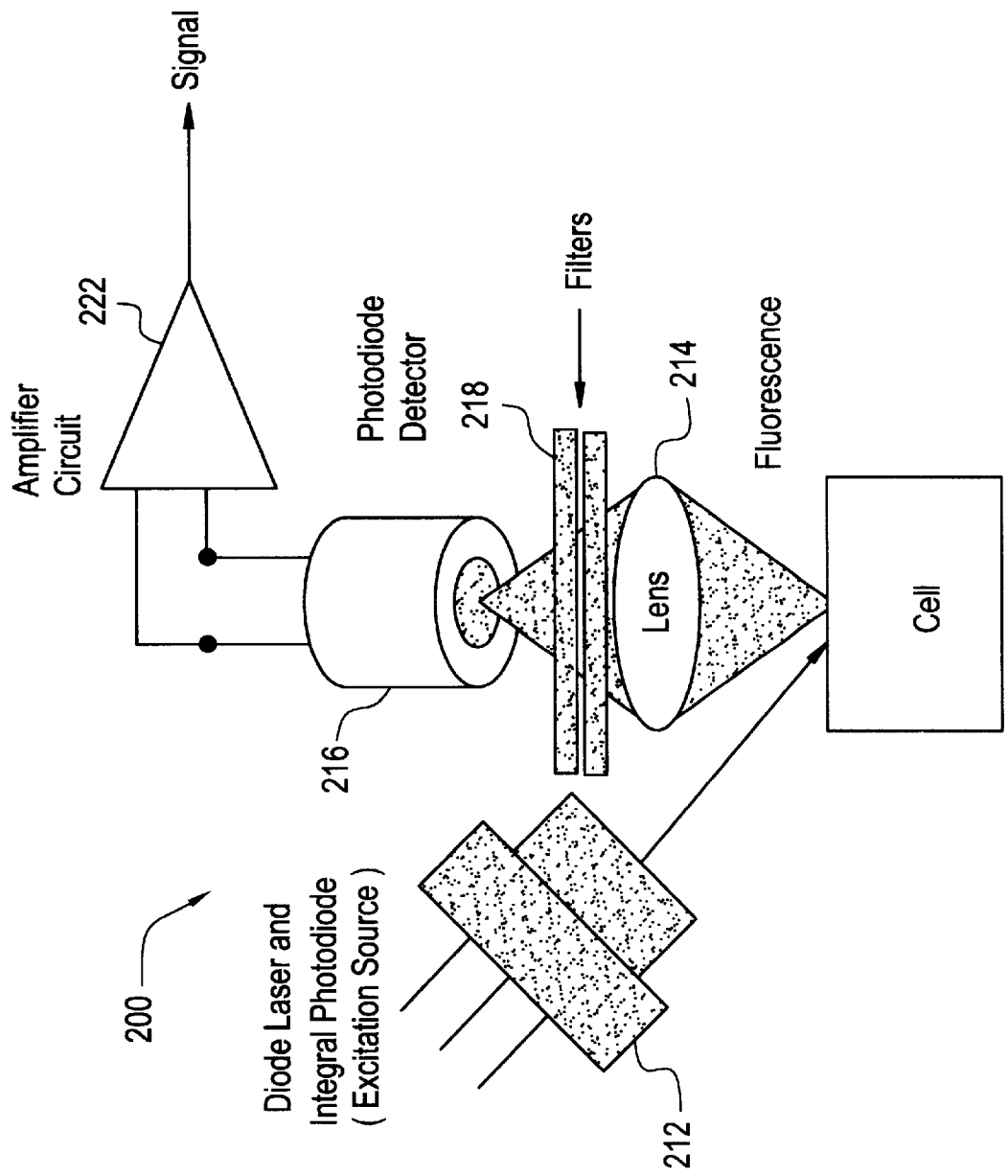
FIG. 5 illustrates a schematic diagram of an embodiment of a fluorometer used for the detection of surface fluorescence from turbid samples or turbid sample streams.

FIG. 5 illustrates a solid-state fluorometer 200 for detecting surface fluorescence. FIG. 5 shows a diode laser 212 with integral photodiode used as an excitation source. However, a light emitting diode focused by a lens could, as well, be implemented.

In ceramics applications, the solid-state fluorometer instrument 200 in the surface fluorescence configuration may monitor the concentration of fluorescence molecules in ceramic slurries. Applications within ceramic slurries include monitoring of treatment dosages; measurement of mixing times in batch mixing vessels; determination of batch contamination from ball mills and other mixing vessels; and, efficiency of transfer from ball mills to mixing tanks.

FIG. 2 illustrates the use of the invention in a surface fluorescence embodiment to monitor the concentration of fluorescein in a ceramic slurry.

Furthermore, the solid-state fluorometer instruments 10 and 200 may be used in applications including process control and monitoring and determination of treatment dosage via direct monitoring of fluorescent tagged polymers, particularly in specific chemical applications. U.S. Pat. No. 5,171,450 the disclosure of which is incorporated herein by reference, discloses the application of fluorescent tagged polymers.

It should be understood that the solid-state fluorometer instruments 10 and 200 are capable of performing any function of the existing technology provided that a suitable fluorophore is available which absorbs in the range accessible with diode lasers or light emitting diodes.

The capability for multi-analyte analysis and monitoring is achieved due to the fact that the LED's and diode lasers are extremely small, and several of these can be stacked so that multiple analyses with one sample cell can be performed. Silicon photodiode detectors are also small, and a compact instrument capable of detecting multiple tracer molecules simultaneously is possible. Furthermore, the small size and portability of the present invention makes multiple site analysis practical. The capability to monitor the system influent and effluent makes feed-forward as well as feedback control more convenient.

Because diode lasers and LEDs are monochromatic, directional light sources, when used in combination with a suitable tracer molecule, they may give lower detection limits than those achievable using current technology. Improved detection limits allow the use of lower tracer molecule concentrations.

Diode lasers are also capable of being pulsed at high frequencies. With gated detection, pulsed operation allows different fluorophores that have distinct fluorescence lifetimes, but the same or similar absorption/emission spectra, to be resolved. This aids in multi-analyte monitoring. This sort of pulsed operation also permits quantitative detection of non-fluorescing molecules that cause changes in the lifetime of fluorescing tracer molecules. Furthermore, time-resolved fluorescence is capable of differentiating bound versus unbound fluorophores.

Solid-state light sources are intrinsically more reliable than conventional gas discharge lamps used in known fluorometers. Additionally, diode lasers have integral photodiodes for stabilization of their light emission, eliminating the need for mechanical light chopping. This further leads to improved reliability. Unlike conventional gas-discharge lamps, diode lasers and LEDs operate on less than ten volts. This is an advantage in harsh, industrial settings where high humidity can lead to electrical arcing and instabilities in high voltages. The simple design of the solid-state fluorometer instrument 10 (e.g. all solid-state components, no moving parts or high voltage power supply) permits instruments that are portable, smaller and more reliable than existing technology.

Because the solid-state instrument 10 uses small light sources and detectors and does not require high voltage power supplies, it may be constructed to be palm-sized and battery operated as set forth above. As a result, portability of the instrument 10 aids individuals making fluorescence measurements with the same instrument 10 at a variety of sample points.

The implementation of lasers, which are coherent light sources, allows them, via the coherence, to be more easily and efficiently coupled into fiber optics. The use of fiber optics allows the instrument 10 to be constructed with a probe that can conveniently be inserted directly into a ceramic slurry. This direct contact with the slurry may have advantages in terms of performance (less light scatter and better signal-to-noise) and reliability (no glass flow cell to break).

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

What is claimed is:

1. A method for monitoring concentration of chemicals in ceramic slurries and powders having an external surface, the method comprising the steps of:
   providing an instrument including an excitation source that directs light to the surface of slurry or powder;
   detecting fluorescence excited by light exciting fluorescent tracer molecules on the surface of the slurry or powder; and
   producing an output signal proportional to the fluorescence wherein the fluorescence is further proportional to the concentration of the fluorescent tracer on the surface of the slurry or powder wherein if the concentration of the fluorescent tracer molecules is proportional to non-fluorescing chemical treatments or additives, then the concentration of the chemical treatments or additives can be monitored.

2. The method of claim 1 further comprising the step of:
   providing a filter to reject the wavelengths of light produced by the excitation source before detecting the fluorescence.

3. The method of claim 1 further comprising the step of:
   amplifying the output signal indicative of the fluorescence.

4. The method of claim 1 wherein the excitation source is a diode laser.

5. The method of claim 1 wherein the excitation source is a solid state diode laser with an integral photodiode.

6. The method of claim 1 wherein the excitation source is a light-emitting diode.

7. The method of claim 1 further comprising the step of:
   providing power to the instrument such that the power allows for portability of the instrument.

8. The method of claim 1 wherein the excitation source is a high-brightness blue light-emitting diode operating at forward currents greater than 20 mA.

9. The method of claim 1 further comprising the step of:
   separating the excitation source from a point at which detecting occurs such that the components are approximately at a 45° angle with respect to each other; and
   placing both the excitation source and detector facing the same side of the cell, and separating the excitation source from a point at which detection occurs such that the angle formed between the line connecting the light source to the surface of the cell and the line connecting the point at which detection occurs to the front surface of the cell for a 45° angle.

10. The method of claim 1 further comprising the step of:
    stacking multiple excitation sources and detectors to measure a corresponding umber of multiple analytes in the sample stream.

11. The method of claim 1 further comprising the step of:
    controlling treatment dosage to the sample stream based on the concentration of molecules detected by the instrument.

12. The method of claim 1 further comprising the step of:
    monitoring the output signal continuously and in real time to determine the concentration of molecules.

13. The method of claim 1 further comprising the step of:
    detecting leakage to or from the sample stream by detecting the concentration of molecules into or from a process, respectively.

14. The method of claim 6, wherein the light emitting diode emits a light having a wavelength of from about 370 nm to about 500 nm.

15. The method of claim 4, wherein the laser emits a light having a wavelength of from about 635 nm to about 1600 nm.

16. The method of claim 1, further comprising a fiber optic cable directing the light from the excitation source through the sample to the detector.

17. A method for monitoring concentration of chemicals in ceramic slurries containing solid components, the method comprising the steps of:
    centrifuging the solid components from a slurry sample to create a precipitate and a supernatant;
    providing an instrument including an excitation source that directs light through the supernatant; detecting fluorescence produced by the light exciting fluorescent tracer molecules in the supernatant; and producing an output signal proportional to the fluorescence wherein the fluorescence is further proportional to the concentration of fluorescent tracer molecules in the original slurry wherein if the concentration of the fluorescent tracer molecules is proportional to non-fluorescing chemical treatments or additives, then the concentration of the chemical treatments or additives can be monitored.

18. A method for monitoring concentration of chemical treatments or additives in ceramic slurries and powders having an external surface, the method comprising the steps of:

providing an instrument including an excitation source that directs light to the surface of the slurry or powder;

detecting fluorescence excited by light exciting fluorescent tagged organic additive molecules on the surface of the slurry or powder; and producing an output signal proportional to the fluorescence wherein if the fluorescence is further proportional to the concentration of the fluorescent tagged organic additive molecules on the surface of the slurry or powder, then the concentration of the chemical treatments and additives can be monitored.

19. A method for monitoring concentration of chemical treatments and additives in a ceramic slurry sample, the method comprising the steps of:

centrifuging solid components from a slurry sample to produce supernatant and a solid component, providing an instrument including an excitation source that directs light through the supernatant;

detecting fluorescence excited by light exciting fluorescent tagged organic additive molecules in the supernatant; and producing an output signal proportional to the fluorescence wherein if the fluorescence is further proportional to the concentration of the fluorescent tagged organic additive molecules in the original slurry, then the concentration of the chemical treatments and additives can be monitored.

* * * * *